United States Patent

Van Hijningen et al.

Patent Number: 5,268,748
Date of Patent: Dec. 7, 1993

[54] ARRANGEMENT FOR MEASURING THE REFLECTION AND/OR TRANSMISSION OF AN OBJECT

[75] Inventors: Nicolaas C. J. A. Van Hijningen; Cornelis J. M. Van Nimwegen, both of Eindhoven; Johannes A. Th. Verhoeven, Maarheeze, all of Netherlands

[73] Assignee: U. S. Philips Corporation, New York, N.Y.

[21] Appl. No.: 834,025

[22] Filed: Feb. 11, 1992

[30] Foreign Application Priority Data

Feb. 13, 1991 [NL] Netherlands .................... 9100248

[51] Int. Cl.⁵ .................... G01N 21/55; G01N 21/59
[52] U.S. Cl. .................... 356/445; 356/432; 356/435; 356/73; 250/572
[58] Field of Search ............... 356/432, 433, 434, 435, 356/440, 444, 445, 448, 73; 250/572

[56] References Cited

U.S. PATENT DOCUMENTS 4,297,587 10/1981 Baker .................... 250/563
4,298,801 11/1981 Heitman .................... 250/447

FOREIGN PATENT DOCUMENTS 0002088 11/1978 European Pat. Off.

Primary Examiner—Vincent P. McGraw
Assistant Examiner—LaCharles P. Keesee
Attorney, Agent, or Firm—David R. Treacy

[57] ABSTRACT

An arrangement for measuring the reflection and/or transmission of an object comprises a frame 1, a carrier 7 for the object, a radiation source 15 and a detector unit. The detector unit, which comprises one or more radiation-sensitive detectors 17A, 17B may be arranged on a holder 13 which is pivotable about a pivotal axis 13a. A slide 5, which is movable parallel to the pivotal axis, may be provided for moving the carrier and the detector unit rectilinearly towards and away from one another.

14 Claims, 1 Drawing Sheet

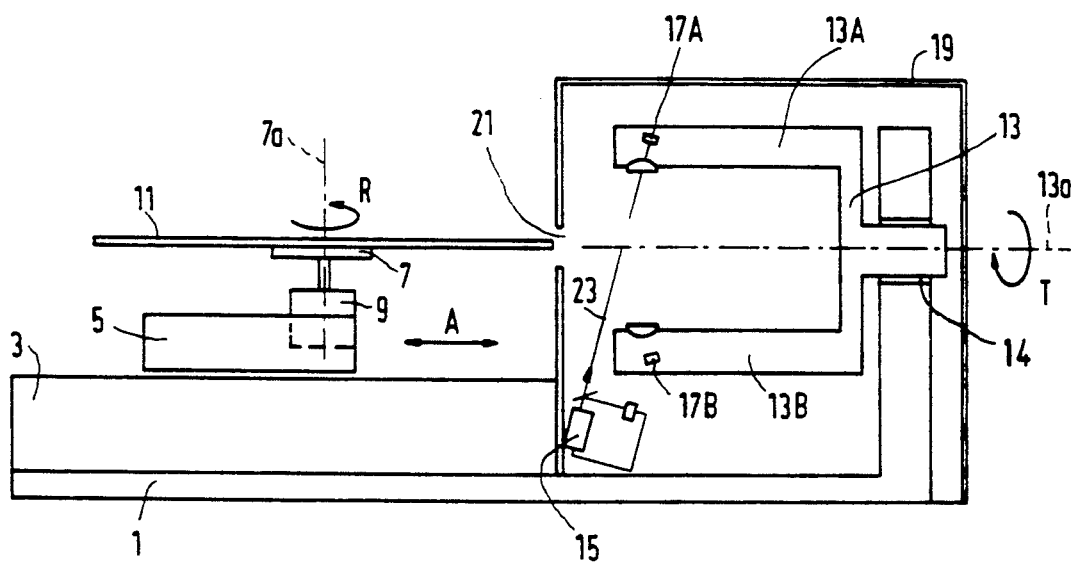

ARRANGEMENT FOR MEASURING THE REFLECTION AND/OR TRANSMISSION OF AN OBJECT

BACKGROUND OF THE INVENTION

The invention relates to an arrangement for measuring the reflection and/or transmission of an object, the arrangement comprising a frame, a carrier for the object, a radiation source and a detector unit.

Such an arrangement is known from DE-A-31 08 344 (herewith incorporated by reference) to which U.S. Pat. No. 4,297,587 corresponds. The known arrangement is suitable for measuring reflection and/or transmission properties of ribbon-like products. To this end the arrangement comprises a guide means for continuously moving the ribbon-like product, a laser source with a rotatable polygonal mirror for iteratively aiming a laser beam at the moving ribbon-like product, and a stationarily arranged detector unit. The detector unit comprises radiation-sensitive detectors disposed at one side or at both sides of the ribbon-like product, depending on the measurement to be carried out. The known arrangement further comprises a stabilised system with one or more sensors for the calibration of the arrangement.

SUMMARY OF THE INVENTION

It is an object of the invention to simplify the arrangement of the type defined in the opening paragraph mechanically and optically in such a manner that no additional sensors are needed for the calibration of the arrangement.

To this end the arrangement in accordance with the invention is characterized in that the detector unit and the carrier are mutually pivotable relative to a pivotal axis, means being provided for moving the carrier and the detector unit towards and away from one another in a plane containing the pivotal axis. Said means enable the object to be measured and the detector unit to be brought into a correct position relative to one another, the measurement position. Independently of the measurement to be carried out, i.e. reflection measurements, transmission measurements or combined measurements, a radiation-sensitive element of the detector unit can be positioned opposite the radiation source to calibrate the arrangement before the object to be measured is brought in the measurement position. For practical reasons it is attractive to arranged the detector unit on a holder which is pivotable about the pivotal axis. For reasons of construction engineering it is also attractive to construct said means as a slide which is movable parallel to the pivotal axis.

An embodiment of the arrangement in accordance with the invention is characterized in that the holder, which is of fork-shaped construction, comprises two limbs which extend substantially to the pivotal axis and which each carry a radiation-sensitive detector, the two detectors being disposed opposite one another. This embodiment is very suitable for the simultaneous measurement of reflection properties and transmission properties of an object, one of the detectors being situated at one side and the other detector being situated at the other side of the object during the measurement. Before the object to be measured is arranged between the limbs of the holder each of the detectors can be positioned opposite the radiation source for the purpose of calibration by a pivotal movement of the holder. After the calibration the object to be measured can be arranged between the detectors, after which the desired measurements can be performed.

A practical embodiment is characterized in that the holder is pivotable through at least 180 degrees relative to the radiation source.

The arrangement is very suitable for measuring the reflection and/or transmission of a disc-shaped object, in particular an optical disc, such as an LV-disc, CD or DOR-disc, or a semi-finished optical disc, for example a polycarbonate substrate provided with a layer structure. The measured reflection and/or transmission value may provide an indication of the quality of the tested object. For measuring the reflection and/or transmission of disc-shaped objects the arrangement in accordance with the invention is preferably characterized in that the carrier is a turntable which is rotatable about an axis of rotation which is oriented transversely of the pivotal axis. This enables the measurements to be performed at a predetermined radius of the disc-shaped object.

A constructionally simple embodiment of the arrangement in accordance with the invention is characterized in that the holder is supported in the frame and the turntable is arranged on the slide.

The arrangement in accordance with the invention has been designed in such a way that it is convenient to use and easy to calibrate, yet enabling the measurements to be performed with a high accuracy. Moreover, the operation of the arrangement is independent of the wavelength of the radiation emitted by the radiation source.

BRIEF DESCRIPTION OF THE DRAWING

The invention will now be described in more detail, by way of example, with reference to the drawing, in which the FIGURE shows diagrammatically an embodiment of the arrangement in accordance with the invention.

DESCRIPTION OF THE PREFERRED EMBODIMENT

The arrangement in accordance with the invention shown in the drawing comprises a frame 1 with a rectilinear guide means 3 for a slide 5. The slide 5, which is movable in the directions indicated by the double arrow A, is driven by an electric-motor unit, for example a linear motor or rotary motor, known per se, provided with a transmission mechanism. The slide 5 carries a turntable 7 which is rotatable about an axis of rotation 7a, which can be driven by a rotary motor 9 and which serves as a carrier for a disc-shaped object 11. In the present example the object 11 is a 12" DOR-disc having an information surface at both sides.

The arrangement in accordance with the invention shown herein further comprises a fork-shaped holder 13, which is pivotable about a pivotal axis 13a extending parallel to the direction of movement A of the slide 5 and which has two limbs 13A and 13B which extend parallel to the pivotal axis. The holder 13 is supported in the frame 1 by means of a bearing 14 and can be driven in the pivoting direction T by an electric motor, not shown.

The present arrangement further comprises a radiation source 15, specifically a laser source, and a detector unit which in the present example comprises two radiation-sensitive sensors or detectors 17A and 17B, and which may be provided with lenses arranged on the respective limbs 13A and 13B of the holder 13. The radiation source 15 and the holder 13 are accommodated in a housing 19 having a loading slot 21.

The radiation source 15 is capable of emitting a parallel radiation beam having a wavelength of, for example 780 nm, which beam is used both for calibrating the arrangement and for measuring the reflection and transmission of the optical disc 11. During calibration the carrier 7 is in the position shown and the radiation beam 23 is incident on the detector 17A on the limb 13A. After the calibration of the radiation source and the detector 17A the carrier is pivoted through 180 degrees about the pivotal axis 13a, causing the detector 17B situated on the limb 13B opposite the detector 17A to be positioned in the path of the radiation beam 23. After the calibration of the radiation source 15 and the detector 17B, in order to carry out the measurements, the slide 5 is moved rectilinearly towards the housing 19 to interpose the optical disc between the detectors 17A and 17B, and the carrier 17 is given a rotation R. The degree of reflection and transmission of the radiation by the optical disc 11 can now be measured at one or more radii by means of the detectors 17A and 17B respectively. After the measurement the optical disc 11 is removed from the housing 19 via the slot 21 by moving the slide 5.

The shown arrangement in accordance with the invention forms part of a measurement unit, which may further comprise a personal computer with suitable software for the processing of the measured reflection and transmission values, a monitor and a printer. The measurements thus carried out provide indications of the optical properties if the tested disc-shaped object.

Obviously, the invention is not limited to the arrangement shown in the drawing. For example, the turntable may be supported in the frame and the fork-shaped holder may be arranged on the slide. Moreover, instead of a linearly movable slide a pivotal arm may be used. It is then possible, for example, to arrange the carrier on the pivotal arm.

We claim:

1. An arrangement for measuring the reflection and/or transmission of an object, comprising:
    a frame, and a radiation source fixed to said frame,
    a carrier for said object, and means for causing relative movement between said carrier and said frame and radiation source, and
    a radiation-sensitive detector unit,
    characterized in that said radiation source and said detector unit are mounted to be pivotal with respect to each other about a pivotal axis,
    said carrier and said detector unit are mounted to be pivotal with respect to each other about said pivotal axis, and
    said means for causing relative movement moves the carrier and said holder towards and away from one another in a plane containing said pivotal axis.

2. An arrangement as claimed in claim 1, characterized in that the detector unit is arranged on a holder which is pivotable about the pivotal axis.

3. An arrangement as claimed in claim 2, characterized in that the means comprise a slide which is movable parallel to the pivotal axis.

4. An arrangement as claimed in claim 2, characterized in that the radiation source and the holder are accommodated in a housing having a loading slot situated opposite the carrier.

5. An arrangement as claimed in claim 2, characterized in that the holder is supported in the frame and the turntable is arranged on the slide.

6. An arrangement as claimed in claim 2, characterized in that the carrier comprises a turntable which is rotatable about an axis of rotation which is oriented transversely of the pivotal axis.

7. An arrangement as claimed in claim 2, characterized in that the holder is pivotable through at least 180 degrees relative to the radiation source.

8. An arrangement as claimed in claim 1, characterized in that the carrier comprises a turntable which is rotatable about an axis of rotation which is oriented transversely of the pivotal axis.

9. An arrangement as claimed in claim 1, characterized in that the means comprise a slide which is movable parallel to the pivotal axis.

10. An arrangement for measuring the reflection and/or transmission of an object, comprising:
    a frame, and a radiation source fixed to said frame,
    a carrier for said object, and means for causing relative movement between said carrier and said frame and radiation source, and
    a radiation-sensitive detector unit,
    characterized in that the arrangement further comprises two said radiation-sensitive detector units, and
    a fork-shaped holder mounted to be pivotal with respect to said frame about a pivotal axis, and having two limbs which extend on opposite sides of said axis, each of said limbs carrying a respective one of said radiation-sensitive detectors, the two detectors being disposed opposite one another, and
    said means for causing relative movement moves the carrier and said holder towards and away from one another in a plane containing said pivotal axis.

11. An arrangement as claimed in claim 10, characterized in that the holder is pivotable through at least 180 degrees relative to the radiation source.

12. An arrangement as claimed in claim 11, characterized in that the carrier comprises a turntable which is rotatable about an axis of rotation which is oriented transversely of the pivotal axis.

13. An arrangement as claimed in claim 11, characterized in that the holder is supported in the frame and the turntable is arranged on the slide.

14. An arrangement as claimed in claim 12, characterized in that the radiation source and the holder are accommodated in a housing having a loading slot situated opposite the carrier.

* * * * *